United States Patent [19]
Hu et al.

[11] Patent Number: 5,744,360
[45] Date of Patent: Apr. 28, 1998

[54] METHODS FOR HARVESTING ADIPOSE TISSUE CONTAINING AUTOLOGOUS MICROVASCULAR ENDOTHELIAL CELLS

[75] Inventors: Can B. Hu, Irvine; Keith E. Myers, Lake Forest; Robert C. Peterson, Dove Canyon, all of Calif.

[73] Assignee: Baxter International Inc., Deerfield, Ill.

[21] Appl. No.: 647,155

[22] Filed: May 9, 1996

Related U.S. Application Data

[63] Continuation of Ser. No. 270,073, Jul. 1, 1994, abandoned.

[51] Int. Cl.$^6$ .............................. C12N 5/00; A61N 1/30; A61B 17/20; A61M 1/00
[52] U.S. Cl. .................... 435/366; 435/325; 604/19; 604/22; 604/27; 604/28; 604/30; 604/35
[58] Field of Search ................. 435/240.2, 283.1, 435/325, 366; 604/19, 22, 27, 28, 30, 35

[56] References Cited

U.S. PATENT DOCUMENTS

| | | | |
|---|---|---|---|
| 3,654,914 | 4/1972 | Franklyn | 128/1 R |
| 4,753,634 | 6/1988 | Johnson | 604/35 |
| 4,792,327 | 12/1988 | Swartz | 604/22 |
| 4,815,462 | 3/1989 | Clark | 606/170 |
| 4,834,703 | 5/1989 | Dubrul et al. | 604/48 |
| 4,857,063 | 8/1989 | Glenn | 604/317 |
| 4,883,755 | 11/1989 | Carabasi et al. | 435/240 |
| 4,886,492 | 12/1989 | Brooke | 604/49 |
| 4,925,450 | 5/1990 | Imonti et al. | 604/240 |
| 5,035,708 | 7/1991 | Alchas et al. | 623/1 |
| 5,052,999 | 10/1991 | Klein | 604/19 |
| 5,102,410 | 4/1992 | Dressel | 606/15 |
| 5,112,302 | 5/1992 | Cucin | 604/35 |
| 5,181,907 | 1/1993 | Becker | 604/22 |
| 5,236,414 | 8/1993 | Takasu | 604/22 |
| 5,261,612 | 11/1993 | Ftaiha | 241/2 |
| 5,269,316 | 12/1993 | Spitalny | 128/754 |
| 5,295,980 | 3/1994 | Ersek | 604/272 |
| 5,338,294 | 8/1994 | Blake, III | 604/38 |
| 5,372,945 | 12/1994 | Alchas et al. | 435/267 |
| 5,419,761 | 5/1995 | Narayanan et al. | 604/22 |
| 5,514,086 | 5/1996 | Parisi et al. | 604/22 |
| 5,527,273 | 6/1996 | Manna et al. | 604/22 |
| 5,569,178 | 10/1996 | Henley | 604/22 |

FOREIGN PATENT DOCUMENTS

| | | |
|---|---|---|
| 001718 | 10/1977 | European Pat. Off. . |
| 190000A2 | 1/1985 | European Pat. Off. . |
| 331313A1 | 2/1988 | European Pat. Off. . |
| 315557 | 5/1989 | European Pat. Off. . |
| 0 399 340 | 11/1990 | European Pat. Off. . |
| 512769 | 3/1991 | European Pat. Off. . |
| 509131A1 | 4/1991 | European Pat. Off. . |
| 2581546 | 5/1985 | France . |
| 1273387 | 9/1969 | United Kingdom . |
| 10405556 | 9/1973 | United Kingdom . |
| WO 81/02523 | 9/1981 | WIPO . |

*Primary Examiner*—Leon B. Lankford, Jr.
*Assistant Examiner*—Christopher R. Tate
*Attorney, Agent, or Firm*—Guy Cumberbatch; Raymond Sun

[57] ABSTRACT

Disclosed herein are methods for harvesting adipose tissue so as to preserve an increased population of viable microvascular endothelial cells. Adipose tissue containing microvascular endothelial cells is harvested using a collection apparatus incorporating an elongate cannula having apertures with tissue cutting edges. A sub-ambient pressure is applied to a lumen in the cannula to draw the adipose tissue through the aperture where it is then severed using the cutting edge to disrupt the connective adipose matrix. This harvesting provides a cleaner, more homogeneous sample of adipose tissue, thereby increasing the population of viable microvascular endothelial cells obtained through further processing. Rapid and easy methods for the further homogenization of the harvested adipose tissue are also disclosed.

19 Claims, 2 Drawing Sheets

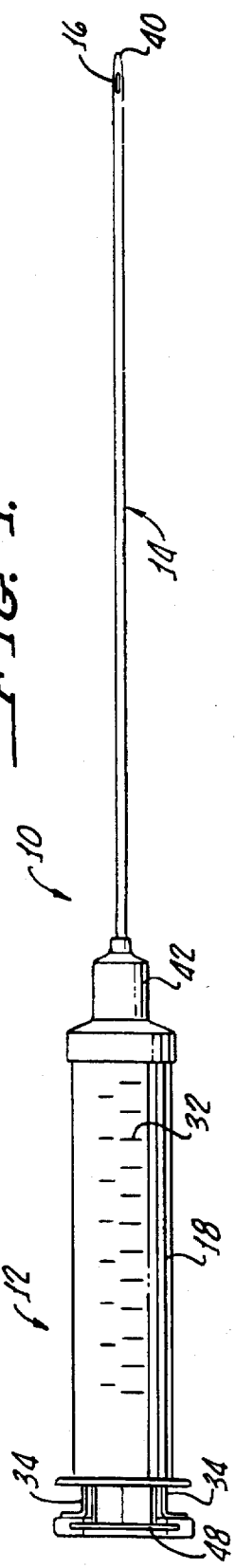
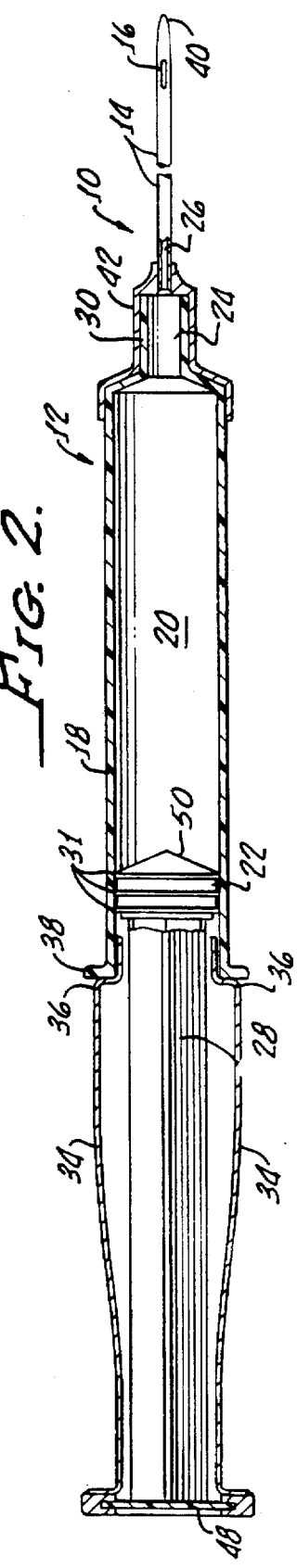
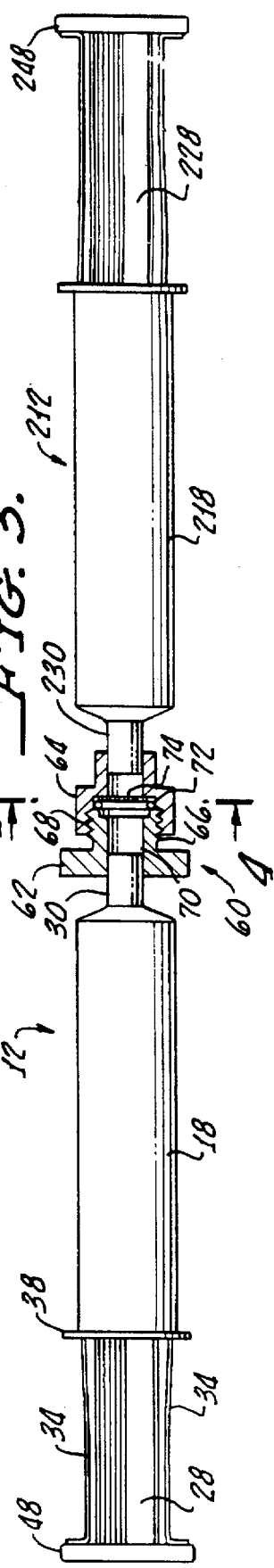

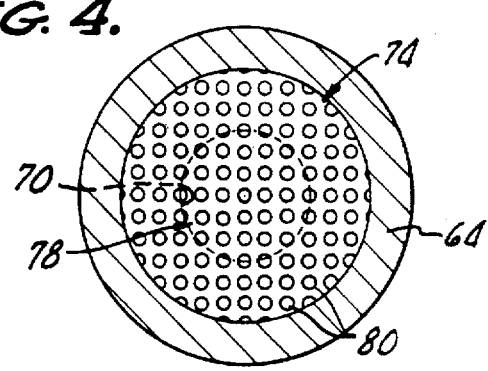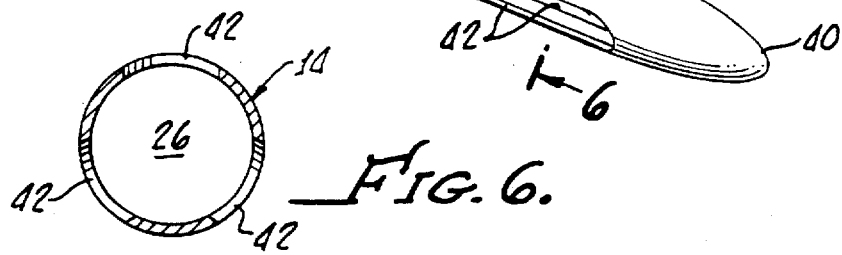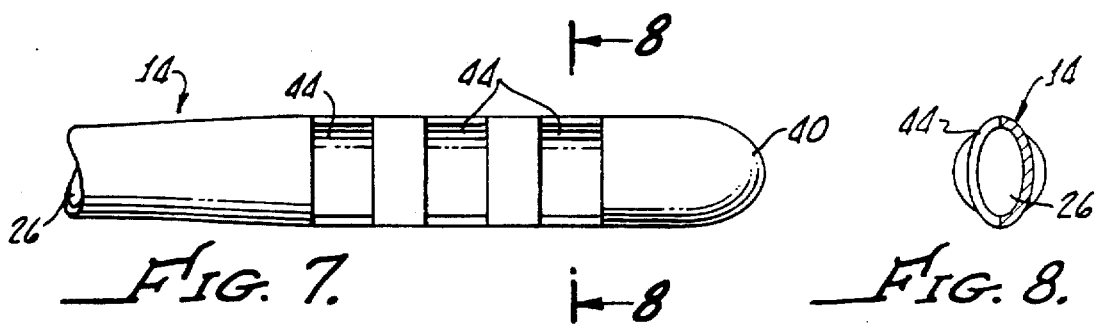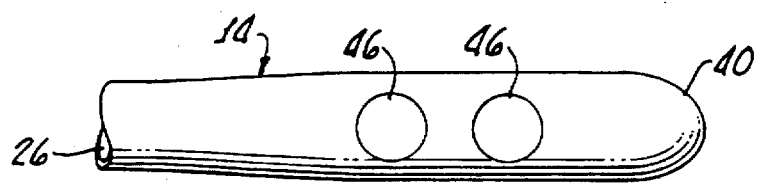

METHODS FOR HARVESTING ADIPOSE TISSUE CONTAINING AUTOLOGOUS MICROVASCULAR ENDOTHELIAL CELLS

RELATED APPLICATION

This is a continuation of U.S. patent application Ser. No. 08/270,073, filed Jul. 1, 1994, now abandoned.

FIELD OF THE INVENTION

The present invention is directed to a method for the harvesting of microvascular endothelial cells. More particularly, the present invention relates to a method for the collection of adipose tissue and the initial refinement of microvascular endothelial cells for deposition on the surface of synthetic prosthetics.

BACKGROUND OF THE INVENTION

Arteriosclerotic vascular disease is a leading cause of death throughout the world. While sophisticated medical techniques such as arterial endarterectomy and percutaneous balloon dilatation are being applied more and more often to treat pathologic stenotic occurrences, quite often the most effective therapy is the surgical removal of the occluded section of the vessel. In such cases, the restoration of blood flow to ischemic tissue depends on the implantation of a vascular graft.

Although autologous vascular tissue is the most suitable material for use in such grafts, prior surgical intervention and advanced vascular disease often limit the availability of such tissue. Accordingly, it has become common in recent years to implant vascular grafts fabricated of synthetic materials. While commercially available synthetic grafts are extremely durable and may be used to successfully restore blood flow to occluded tissue, associated thrombogenic complications reduce their effectiveness. In particular, smaller diameter vascular grafts tend to become dysfunctional as they are blocked by the normal clotting mechanisms. Specifically, the synthetic surface of the graft promotes the deposition of fibrin leading to associated cellular adhesion and occlusion of the vessel. Consequently, the long term prognosis for non-coated synthetic grafts is relatively poor.

To circumvent the problems associated with non-coated synthetic vascular grafts, procedures are being developed for lining prosthetics with human endothelial cells to produce a non-thrombogenic cell surface such as exists in native human vessels. The endothelial lining of natural blood vessels is a highly complex, multifunctional cell surface which interacts with both the blood and the underlying vessel wall components to maintain physiological homeostasis. Tests with animals have shown that the deposition of a functional large vessel endothelial cell lining on the interior surface of synthetic vascular grafts decreases the formation of thrombogenic occlusions and minimizes the disruption of blood flow through the vessel. However, harvesting a sufficient number of large vessel cells from a donor is difficult at best.

Recent advances in molecular biology and tissue culture have allowed the isolation and subsequent propagation of large vessel endothelial cells. In practice, the use of cultured large vessel endothelial cells is expensive, complicated and subject to inherent limitations. One problem is that cell culture techniques are highly technical requiring trained personnel and the use of specialized equipment under laboratory conditions. Yet, even under the best of conditions, the yield of cultured large vessel endothelial cells may be low. Moreover, typical seeding procedures using cultured cells require the use of specialized media under complex conditions to assure the complete and even deposition of endothelial cells on the synthetic surface of the graft.

In addition, cultured cells are generally not derived from the patient receiving the graft and, accordingly, may precipitate a wide range of immunological complications. If the immune response of the patient is not attenuated, the transplanted endothelial cells will likely be attacked and stripped from the surface of the graft by the body's defenses. Conversely, if the patient's immune system is artificially suppressed it may lead to life-threatening, opportunistic infections.

In view of these and other complications associated with the use of large vessel endothelial cell treatments of prosthetic devices, alternative methods of reducing the inherent thrombogenicity of synthetic materials have been developed. In particular, it was quickly recognized that human microvascular endothelial cells could be effectively used to render synthetic grafts non-thrombogenic.

Microvascular endothelial cells are derived from capillaries, arterioles and venules and are present in an abundant supply in most body tissues. While endothelial cells may be isolated from tissues such as brain, lung, retina, adrenal glands, liver and muscle tissue, the use of fat tissue as a source for these cells is preferred due to its abundance, availability and because its removal should not adversely affect the patient being treated. Quite often, microvascular endothelial cells are present in concentrations of $10^6$ cells per gram of fat or higher, providing an ample source of materials for high density deposition procedures. Moreover, as the microvascular cells used to treat the synthetic graft are usually autologous, that is, taken from the recipient of the vascular prosthesis, immunological complications may be obviated.

Typically, microvascular endothelial cells are isolated from autologous adipose tissues such as perinephric fat, subcutaneous fat, omentum, or fat associated with the peritoneal cavity. Harvesting usually takes place under sterile conditions with the required amount of fat removed in one procedure. The collected tissue may then be washed before being transferred to a buffered digestive solution generally containing proteolytic enzymes such as collagenase, papain, trypsin, and mixtures thereof.

The adipose tissue is digested at 37° C. for a selected period to disrupt the connective matrix and disperse the cellular components including microvascular endothelial cells. Following digestion, the cellular components may be separated by low speed centrifugation to provide a cell-rich pellet. The pellet may be washed and used in the deposition procedure or purified further using a continuous gradient. In either case, purified cells are diluted in buffer and subsequently incubated with the synthetic prosthesis to provide endothelialized surfaces.

Commonly, collection of the desired adipose tissue involves the use of a suction pump connected to a collection apparatus having a needle or cannula. For example, U.S. Pat. Nos. 5,035,708 and 4,834,703, incorporated herein by reference, disclose the collection of adipose tissue using a suction pump to provide the necessary vacuum. However, such collection devices and associated methods tend to employ strong, uncontrollable suction that is extremely rough on the microvascular cellular components of the collected tissue. The resulting disruption of the relatively fragile cellular membranes can substantially lower the viability of the harvested cells. This, in turn, dramatically reduces the efficiency of the deposition process. While such collection procedures may provide sufficient adipose tissue, samples collected using such techniques generally require several additional labor-intensive preparatory steps to assure an adequate concentration of relatively pure microvascular endothelial cells for eventual deposition.

Further, source tissue collected using suction pumps is often relatively dirty, contaminated with unwanted body fluids and non-adipose cellular debris. Rather than obtaining translucent, white samples as seen in relatively pure adipose tissue, samples collected using pump-generated vacuums often appear bloody, with concentrations of connective or membrane tissue dispersed within the fat.

The incorporated contaminants interfere with each step of microvascular endothelial cell isolation including the initial homogenization and preparation of the collected sample for digestion. Moreover, such contaminants directly inhibit the enzymatic activity of the proteolytic enzymes leading to incomplete digestion of the sample and a corresponding reduction in the yield of non-adipose cellular components subsequently obtained by centrifugation. Finally, those cells which are collected and pelleted contain increased level of non-endothelial components. The use of such contaminated pellets further lowers the efficiency of the cell deposition procedure and interferes with the homogeneous layering of endothelial cells on the prosthetic surface. Consequently, the patient may have to endure more extensive liposuction than would otherwise be required in order to provide a sufficient number of microvascular endothelial cells.

As the efficiency of the endothelialization process is lowered at each step along the way by contaminants, the importance of starting this procedure with a relatively clean sample is evident. That is, a small increase in the amount of contaminating materials initially collected can dramatically reduce the yield of viable microvascular endothelial cells available for deposition on the surface of the synthetic graft. In addition to increasing the amount of adipose tissue which must be initially collected, the inevitable reduction in cell viability due to contaminating materials must be compensated for by longer deposition times or additional purification steps, both of which reduce the operating efficiency of the entire procedure. This can be particularly detrimental if the cells are to be collected immediately prior to the implantation of the prosthetic device.

Accordingly, a need exists to improve the yield of viable endothelial cells recovered from adipose tissue collected from a patient preparatory to implantation of a synthetic prosthesis. That is, microvascular endothelial cells which are present in a fat specimen should be more efficiently separated from the fat cells, blood cells, connective tissue, and other materials that are present in the specimen, so that a larger number of such endothelial cells are available to be deposited onto the synthetic graft.

In addition to the actual problems associated with the collection of material, the use of a suction pump complicates the operating environment and interferes with the surgeon's ability to freely maneuver the adipose tissue collection apparatus. More particularly, the collection apparatus is usually attached to the vacuum source via thick, unwieldy hoses that severely compromise the maneuverability of the collection tip. Such pumps often do not allow the precise, real time control of the strength of the vacuum at the collection tip, making it difficult to maintain constant, even harvesting of the desired source tissue. This lack of convenience and precise control inevitably results in the aspiration of undesirable tissue, thereby increasing the contaminant level of the samples or resulting in the collection of less preferable adipose tissue containing lower levels of microvascular endothelial cells. Further, vacuum sources, especially those approved for use in medical procedures, are generally complicated instruments that are relatively expensive to maintain.

In view of the deficiencies of the related technology as outlined above, it is an object of the present invention to provide an efficient, cost effective method for the collection of adipose tissue containing microvascular endothelial cells.

It is another object of the present invention to provide a reliable convenient method for the collection of substantially pure adipose tissue containing high levels of microvascular endothelial cells with a minimum of blood cells, connective tissue and other contaminants.

It is still a further object of the present invention to provide a reliable convenient method for the rapid homogenization of adipose tissue to facilitate the subsequent separation of microvascular endothelial cells.

SUMMARY OF THE INVENTION

These and other objectives are achieved by the present invention which, in a broad aspect, is directed to efficient, reliable and cost effective methods for the harvesting of adipose tissue containing identifiable cellular components such as microvascular endothelial cells. More particularly, the present invention is directed to methods of harvesting adipose tissue so as to preserve an increased population of viable endothelial cells using a collection apparatus generally comprising a variable volume container, typically a syringe assembly, attached to an elongated cannula. The elongated cannula, in fluid conducting communication with the variable volume container or syringe, preferably includes apertures appropriately sized and configured to minimize stress placed on cellular components while disrupting the connective matrix of the adipose tissue. That is, by collecting adipose tissue using specifically configured cannular apertures, the yield of endothelial cells may be substantially increased. Further, the collection apparatus is inexpensive, lightweight, easy to manipulate and allows accurate control of the applied suction.

The tissue harvesting methods of the present invention generally begin by inserting at least a portion of the cannula of the collection apparatus into the patient and directing the cannula tip to the area where the adipose tissue is to be collected. Preferably the harvesting procedure is carried out under aseptic conditions. Optionally, a saline solution or other biocompatible liquid may be injected into the collection area of the patient prior to harvesting to loosen the adipose tissue matrix. Following the insertion and positioning of the cannula tip, sub-ambient pressure is generated in the central bore of the syringe by drawing back a displaceable piston affixed to a plunger. If desired the piston may be retained in this withdrawn configuration by a locking mechanism attached to the plunger and designed to interact with the body of the syringe. The locking mechanism frees the hands of the operator and, when combined with the light weight of the collection apparatus provides enhanced maneuverability. In any case, the sub-ambient pressure in the central bore suctions the adipose tissue from the selected collection area, into the disruptive apertures of the cannula, through the cannula body and into the syringe assembly. As the central bore of the syringe fills with collected tissue, the sub-ambient pressure slowly equilibrates. Once the central bore of the syringe is substantially filled with relatively homogeneous adipose tissue the cannula tip is removed from the patient.

Another aspect of the present invention allows for the collected adipose tissue to be readily homogenized and washed with aqueous solutions to remove contaminating matter. Following removal of the cannula tip from the patient, the cannula may be detached from the syringe assembly. A filter, contained in a filter hub, may then be attached to the syringe assembly where the cannula was previously affixed. A second syringe assembly, preferably the same size as the first is then attached to the opposite side of the filter hub. When so joined, the piston of the first syringe assembly is substantially rearward in the syringe and the piston of the second syringe assembly is in a substantially forward position. By using the plungers to displacing the two pistons, the collected fat may be rapidly homogenized as it is forced through the filter which transects the flow path of the sample tissue. Optionally, rinse solutions may be added during the homogenization to separate contaminants from the endothelial cell rich adipose tissue homogenate. After homogenization and rinsing, collected adipose tissue, now substantially free of intact connective tissue and other contaminants, may be transferred to appropriate containers for digestion and further purification.

Additional objects and advantages of the present invention will be apparent from a reading of the following detailed description and exemplary preferred embodiment of the invention taken in conjunction with the appended drawing figures in which like reference numerals denote the same feature or features which are analogous in structure.

BRIEF DESCRIPTION OF THE DRAWINGS

FIG. 1 is a perspective view of an adipose tissue collection apparatus showing attachment of the cannula to a syringe assembly with the plunger in an inserted position;

FIG. 2 is a partial sectional view of an adipose tissue collection apparatus showing the plunger held in a withdrawn position by an exemplary locking mechanism;

FIG. 3 is a partial sectional view of two syringe assemblies interconnected by a filter hub illustrating a configuration of the present invention used for homogenization of harvested adipose tissue;

FIG. 4 is a cross-sectional view taken across line 4—4 of FIG. 3 showing a homogenization filter according to the present invention;

FIG. 5 is a partial perspective view of a tip of a cannula used to provide high yields of microvascular endothelial cells in accordance with the teachings of the present invention;

FIG. 6 is a cross-sectional view taken along line 6—6 of FIG. 5 showing the positioning of the collection apertures adjacent to the tip of the cannula;

FIG. 7 is a partial perspective view of a tip portion of an embodiment of a cannula used to harvest adipose tissue;

FIG. 8 is a cross-sectional view taken along line 8—8 of FIG. 7 illustrating the elliptical shape and positioning of the collection apertures adjacent to the tip of the cannula;

FIG. 9 is a partial perspective view of a tip portion of another alternative embodiment of a cannula used to harvest adipose tissue.

DETAILED DESCRIPTION

Although this invention may be embodied in many different forms, there are shown in the drawings and will be described in detail specific embodiments thereof with the understanding that the present disclosure is to be considered as an exemplification of the principles of the invention and is not intended to limit the invention to the specific embodiments illustrated. In particular, it must be emphasized that the present invention provides for the association of a wide variety of syringe bodies and cannulas beyond those shown in the figures.

Moreover, the present invention may be used to harvest any identifiable cells associated with the adipose tissue matrix and is not limited to the harvesting and isolation of microvascular endothelial cells. As used herein the term "identifiable cellular components" refers to those cells which may be recognized by commonly used immunogenic, chemical or physical separation methods or tests.

Similarly, while the endothelialization of vascular prosthetics is an important object of the present invention, those skilled in the art will appreciate that the cellular products collected may be used to treat other implantable devices. Implants which can be treated to produce an endothelial cell lining or covering include, but are not limited to, intravascular devices such as artificial hearts, valvular prosthetics, and natural or artificial valve leaflets. The collection apparatus and methods of this invention for harvesting endothelial cell rich adipose tissue may be used in the treatment of surfaces comprised of known synthetic materials such as polyester, polytetrafluoroethylene, or fixed and unfixed naturally occurring materials such as veins, arteries, heart valves and other tissues from animal sources, including humans.

Turning now to the figures, FIGS. 1 and 2 show an adipose tissue collection apparatus 10 essentially comprising a variable volume container in the form of syringe assembly 12. Syringe assembly 12 is in fluid tight communication with an elongated cannula 14 having a lumen 26 and at least one collection aperture 16 appropriately configured for the relatively homogeneous collection of adipose tissue containing microvascular endothelial cells. Syringe assembly 12 generally comprises a hollow tubular body 18 defining a central bore 20 having a displaceable piston 22 sealingly disposed therein. Preferably piston 22 is affixed to an elongate plunger 28 which extends through an opening in the rear of hollow tubular body 18. By manually displacing plunger 28, piston 22 may be reversibly moved along the length of central bore 20. Sealing rings 31 ensure that piston 22 maintains good contact with the interior of tubular body 18 as it moves longitudinally. An entrance port 24 at the forward end of hollow tubular body 18 provides for fluid conducting communication between cannula lumen 26 and central bore 20.

Preferably syringe assembly 12 is a Toomey-type syringe (Sherwood Medical Co., St. Louis, Mo.) having a tapered tip 30 defining entrance port 24. While a Toomey-type syringe is preferred due to the ease of switching cannulas or other attachments, syringe assemblies having other types of connection mechanisms such as threaded connectors, catheter tips or luer locks are compatible with the present invention. Typically, hollow tubular body 18 of syringe assembly 12 is formed of an inexpensive, non-reactive material such as polypropylene or other rugged polymer composition. Of course, those skilled in the art will appreciate that the size and fluid capacity of syringe assembly 12 may vary based on the amount of adipose tissue to be collected. However, for obvious reasons it is preferable that syringe assembly 12 be of sufficient volume to harvest the desired amount of adipose tissue in one collection procedure. As the volume of adipose tissue needed to provide the necessary amount of endothelial cells for an average cell deposition procedure is on the order of 20 mls to 50 mls, a preferred syringe volume is approximately 60 mls. Gradations 32 on the sides of most commercially available syringes provide an easy method for monitoring the amount of fat collected.

Optionally, syringe assembly 12 is provided with a locking mechanism 34, attached to plunger flange 48 which reversibly engages annular flange 38 at the rear of hollow tubular body 18 to retain plunger 28 and attached piston 22 in a withdrawn configuration. This configuration is illustrated in FIG. 2. When plunger 28 and piston 22 are in a substantially forward position, as shown in FIG. 1 the inner surface of hollow tubular body 18 will act on shoulders 36 of locking mechanism 34 to maintain it in a closed position. However, when plunger 28 is withdrawn past a certain predetermined point where shoulders 36 are no longer restrained, locking mechanism 34 will spring open due to the elastic memory of the mechanism material. When in an open position, shoulders 36 of locking mechanism 34 will be positioned to engage annular flange 38 as well as plunger flange 48 thereby preventing plunger 28 from reentering hollow tubular body 18. However, plunger 28 may be easily moved to a forward position by manually compressing locking mechanism 34 to reduce the diameter of shoulders 36 where they disengage annular flange 38 and slide easily into hollow tubular body 18. Although various locking mechanisms are compatible with the present invention, one particularly suitable device is sold under the trade name Grazer-Grams Lock (Gram Medical, Costa Mesa, Calif.). In addition to being obtainable for a variety of syringe sizes, these locking mechanisms are also available in a single shoulder embodiment.

The last major constituent of collection apparatus 10 is cannula 14 having a lumen 26, a proximal end and a distal cannula tip 40. Many commercially available cannulas having different lengths and diameters are compatible with the present invention and may be used with various syringe assemblies. Cannulas which are particularly compatible and provide relatively high yields when used in accordance with the teachings herein are sold under the trade name Mercedes (Grams Medical, Costa Mesa, Calif.) and have inner diameters ranging from approximately 1 mm to 8 mm. Particularly preferable inner diameters range from 1.5 mm to 4 mm. While generally formed out of metal alloys such as stainless steel for ease of resterilization and reuse, the surfaces of these cannulas may be coated with biocompatible polymers to reduce stress on the collected cellular components.

While the general configuration of cannula 14 is relatively consistent for the different embodiments i.e. generally elongated with at least one lumen 26, other characteristics of compatible cannulas may vary markedly. For example cannula connection 42, shown in FIGS. 1 and 2 at the proximal end of cannula 14, is adapted to seat on and releasably engage a syringe having a tapered tip 30. Those skilled in the art will appreciate that, as with syringe assemblies, many types of cannula connections are compatible with the teachings of the present invention as long as they are adapted to engage selected syringe assembly 12. For example, cannulas having luer connectors, catheter connectors, threaded connectors and compression fittings may be used for the harvest of adipose tissue as long as they are compatible with the connector of the selected syringe assembly. Moreover, cannulas permanently affixed to a syringe assembly to form a collection apparatus are also within the scope of the present invention and may be used with comparable results.

Another important feature of the cannulas of the present invention which may vary depending on the desires of the operating physician are the configuration and position of the collection apertures. For example, FIGS. 5, 6, 7, 8 and 9 all show different configurations of collection apertures. In accordance with the present invention is desirable that the shape and configuration of the collection apertures impose stresses during harvest which disrupt the macro structures and connective components of the adipose tissue to provide a relatively homogeneous yield. Further the collection apertures should be large enough to resist blocking by any non-disrupted tissue thereby necessitating the removal of the cannula from the patient and interruption of the harvest procedure. Based on such considerations, collection apertures preferably range from 1 mm to 4 mm and more preferably from 1.5 mm to 3 mm.

The aperture configuration of FIG. 5 displays elongated tissue cutting edges on apertures 42 which result in substantially increased cell yields. In contrast, the rounded or less abrupt aperture edges such as those shown in FIGS. 7 and 9, do not appear to provide tissue cutting edges sufficiently disruptive to the connective matrix of the tissue resulting in less homogeneous sample composition and lower cell yield. While tissue cutting aperture configurations disrupt the macro connective structure of the harvested tissue, they do not unnecessarily place stress or shearing forces on the delicate cellular components dispersed within the adipose tissue matrix. While the rounded edges of collection apertures 44 and collection apertures 46 assist in reducing these undesirable shearing forces, they do not provide for the collection of substantially homogeneous tissue and therefore lower the overall cell yield.

Just as various configurations and sizes of collection apertures are compatible with the methods of the present invention, so to are different aperture placement schemes and cannula shapes. For example there is no requirement that the collection apertures be limited to locations near distal cannula tip 40. While such placement may promote sample purity as the collection area can be gauged more accurately, apertures placed further away from the tip may work equally well. Similarly, there is no requirement that cannula 14, and by extension lumen 26 be cylindrical in nature. For example, other, more elliptical, shapes may provide the same cell yield as the perfectly cylindrical shape illustrated in FIG. 6. Accordingly, as with the syringe assemblies, a wide range of cannula shapes, sizes and configurations are with in the scope of the invention and may be chosen based on the preferences of the individual operator.

In any event, once a collection apparatus is selected and assembled, the actual harvesting of the adipose tissue and identifiable cellular components may begin. Preferably the entire procedure is carried out under aseptic conditions. Collection apparatus 10 may be pre-assembled and sterilized ahead of time or may be assembled in the operating area just prior to use. Typically, syringe assembly 12, minus locking mechanism 34, is commercially available in a disposable, presterilized and prepackaged form. Conversely, cannula 14 is typically reusable and has been cleaned, packaged and resterilized on site. Accordingly, following the selection of compatible components which may be releasably engaged, syringe assembly 12 and cannula 14 are usually mated to form collection apparatus 10 just prior to insertion in the patient. At approximately the same time as syringe assembly 12 is attached to cannula 14 optional locking mechanism 34 may be affixed to plunger 28 via plunger flange 48. Preferably, locking mechanism 34 is affixed prior to engaging cannula 14 to reduce the chances of inadvertent sample contamination.

As an optional preliminary step, saline or other biocompatible solutions may be injected into the adipose collection area prior to harvesting the desired material. The introduction of liquids into the area appears to disrupt the adipose matrix and reduce the cohesion of the connective tissue. To assist this disruption the fluid injected tissue may be massaged vigorously or subjected to other external forces. As those skilled in the art will appreciate, the actual volume of saline injected, area of injection and the time of injection before harvesting will depend on the circumstances of the operation such as age and health of the patient, amount of tissue to be harvested and the location of the adipose collection area. Typically several milliliters of solution will be injected approximately thirty minutes to an hour before harvesting is undertaken. A standard syringe and injection needle are used for the procedure. While it appears to improve the homogeneity of the sample recovered, adequate microvascular endothelial cell yields may be obtained without the addition of fluids or the application of external forces prior to harvesting.

When the adipose tissue is considered ready for harvest at least a portion of cannula 14 is inserted in the patient near the adipose tissue to be taken. Given the typical size of cannula 14 and its relatively blunt distal tip 40, a small incision is usually made in the skin of the patient for the insertion. Following insertion, distal cannula tip 40, and more particularly aperture or apertures 16, is maneuvered to the area where the adipose tissue is to be harvested. As previously discussed, the adipose tissue is usually taken from perinephric fat, subcutaneous fat, omentum, or fat associated with the peritoneal cavity. Given the light weight and relatively small size of collection apparatus 10 the operating physician will have little trouble guiding cannula 14 as desired and precisely positioning it in the proper location.

It is important to note that, during the insertion and positioning of cannula 14 in the body of the patient, plunger 28 and displaceable piston 22 are fully inserted in hollow tubular body 18. That is, forward surface 50 of displaceable piston 22 is seated flush against the forward end of hollow tubular body 18 adjacent to entrance port 24. At the same time optional locking mechanism 34 is retained in a closed position by the inner surface of hollow tubular body 18. With displaceable piston 22 in a fully forward position, substantial amounts of fluid and other bodily material are prevented from entering cannula 14 and syringe assembly 12. Displaceable piston 22 is retained in this configuration until cannula 14 is properly positioned and the physician is ready to begin harvesting the adipose tissue surrounding apertures 16.

To initiate harvesting of the microvascular endothelial cell rich adipose tissue sub-ambient pressure is applied to cannula 14. Typically plunger 28 and affixed piston 22 are slowly drawn back through hollow tubular body 18 by the operator. If desired, optional locking mechanism 34 may be engaged with annular flange 38 to maintain the withdrawn configuration and sub-ambient pressure. The increase in sealed volume defined by forward surface 50 of piston 22 and the inner surface of hollow tube body 18 creates sub-ambient pressure in syringe assembly 12. This, in turn, creates a suction in lumen 26 of cannula 14 which is in fluid tight communication with central bore 20 through entrance port 24. Unlike prior art suction pumps which maintained a uniformly high suction force at the collection tip, the present invention provides a gentle sub-ambient pressure which is easily and instantaneously adjustable. Judging by the "feel" of collection apparatus 10, or the appearance of the adipose tissue being harvested, the operator can attenuate the suction applied at apertures 16 by adjusting the amount plunger 28 is withdrawn from hollow tubular body 18. By pushing plunger 18 the suction will be reduced while withdrawing it further (maintaining the sealable deposition of piston 22 hollow tubular body 18) will rapidly increase the suction at the aperture. Alternatively, the operator may simply rely on locking mechanism 34 to maintain a steady suction at apertures 16.

The easily controllable sub-ambient pressure, combined with the favorable tissue cutting characteristics of apertures 16 provide cleaner more homogeneous adipose tissue for processing. Obstructing connective tissue is preferably disrupted while preserving the integrity of the cellular components. Moreover, as the operator is able to easily and efficiently adjust the position of cannula 14, regions of higher contamination may be avoided further increasing the purity of the tissue obtained. Should there be a problem with obstruction of apertures 16 or cannula 14, the operator may simply push plunger 28 slightly forward to apply positive pressure to the cannula and apertures thereby clearing the obstruction. Finally, as the plunger is under direct control of the operator, the amount of adipose tissue collected may be controlled more closely.

Following the harvest of the desired amount of homogeneous adipose tissue and pressure equilibration of collection apparatus 10, cannula 14 is removed from the patient through the initial insertion site preferably maintaining aseptic conditions. As previously discussed the actual amount of adipose tissue collected will depend on a number of factors including number of microvascular endothelial cells needed and the capacity of collection apparatus 10. Typical volumes range from approximately 10 ml to approximately 100 ml with average volumes ranging from about 40 ml to about 60 ml. Of course those skilled in the art will appreciate that smaller or larger volumes may be collected for the purification of microvascular endothelial cells or other cellular components using the methods of the present invention. After cannula 14 is removed from the patient, it is usually disengaged from syringe assembly 12 containing the harvested tissue for cleaning and resterilization.

At this point, the harvested tissue may be processed further or stored for later use. For storage, the tissue is usually removed from syringe assembly 12 by ejecting it through harvesting port 24 into a separate container which may then be chilled. For processing, the collected tissue may be similarly transferred to microvascular cell isolation apparatus such as the one described in copending U.S. patent application Ser. No. 08/086,778, which is incorporated herein by reference. The desired identifiable cellular components will then be separated from the adipose tissue using digestion and the other procedures previously discussed.

Alternatively, in accordance with the teachings of the present invention the harvested adipose tissue may be processed further using syringe assembly 12 for rinsing and homogenization. For example, water or other aqueous solutions could be introduced into central bore 20 with the collected sample and shaken. Afterward the mixture is allowed to settle, preferably in a syringe stand (not shown), and separate. The adipose cells and associated tissue including the overwhelming majority of microvascular endothelial cells will float while connective tissue, red blood cells and other contaminants sink or our solubilized in the aqueous solution. The rinsed adipose cells and associated tissue may then be decanted. Of course the process may be repeated as many times as necessary.

In another procedure the harvested tissue may be homogenized and rinsed at the same time. Referring now to FIG. 3, syringe assembly 12, containing the harvested tissue, is releasably attached to filter hub assembly 60. A second syringe assembly 212, preferably the same size as syringe assembly 12, is releasably attached to the opposite side of filter hub assembly 60. For the purposes of clarity reference numerals previously used for syringe assembly 12 will be used in the following discussion. Corresponding components of syringe assembly 212 will use the same reference numerals with the prefix 2.

In the embodiment shown, syringe assemblies 12 and 212 are Toomey-type syringes having tapered tips 30 and 230 positioned at their respective front ends. However, as previously discussed, many types of connectors are compatible with the teachings of the present invention. Accordingly, any type of tip which is releasably engageable with filter hub assembly 60 may be used.

Filter hub assembly 60 comprises a male hub 62 and a female hub 64 which may be mated using releasably engageable male threads 66 and female threads 68. When so mated, male hub 62 and female hub 64 cooperatively define passage 70. Passage 70 traverses filter hub assembly 60 with openings on opposite faces adapted to releasably engage tapered tip 30 and tapered tip 230 thereby placing syringe assembly 12 and syringe assembly 212 in sealed fluid conducting communication with each other. Filter member 74, shown more clearly in FIG. 4, is positioned axially with respect to passage 70 transecting it as the filter is held in place by compression forces imposed by mated male hub 62 and female hub 64. By transecting passage 70, filter 74 interrupts any flow of tissue or fluid therethrough. Elastic grommet 72, adjacent to filter member 74 ensures that hub assembly 60 is sealingly engaged.

Filter member 74 is a flat, radial disk-like structure having a central portion indicated by arrowed line 78. Multiple filter apertures 80, positioned in central portion 78 traverse the thickness of filter 74 thereby allowing material pass through. Exemplary embodiments use a filter member 74 having an outer diameter of 24 mm with filter apertures 80 having a diameter of approximately 1 mm. FIG. 4 also shows female hub 64 surrounding filter member 74. Of course those skilled in the art will appreciate that other aperture diameters may be employed depending on the amount of homogenization desired.

Typically, filter member 74 is formed of a tough, resterilizable metallic alloy such as stainless steel. However, as previously discussed, the use of metallic components to process adipose tissue may be detrimental to the yield of viable microvascular endothelial cells as metallic alloys have inherently high surface energy. Accordingly, it is preferable if filter 74 is formed of a material having a low surface energy or, if metal is used, that it is coated with a material such as parylene. By low surface energy, it is meant that the materials have a lower electrochemical energy in comparison with metals. Examples of materials having low surface energy and good biocompatability which may be used to practice the present invention include, but are not limited to, polyethylene, parylene, polypropylene, nylon and other fluoropolymers.

While the size and configuration of selected apertures 16 yield a relatively homogeneous sample of adipose tissue, further homogenization to disrupt connective tissue in the adipose matrix may improve cell yield if done gently. As indicated above, collected adipose material is retained in syringe assembly 12 following harvesting. The material may be in its natural, harvested state or rinsed as previously described. Optionally, liquids may be added to the collected material. Filter hub assembly 60, having filter member 74 positioned across passage 70, is releasably engaged to tapered tip 30. Syringe assembly 212 is similarly attached to filter hub assembly 60 on the side opposite syringe assembly 12. When connected in this manner, syringe assembly 12 is in sealed fluid conducting communication with syringe assembly 212 through passage 70.

Plunger 28 is then pushed forward into hollow tubular body 18 to discharge the harvested adipose tissue and any added liquids from harvesting port 24 defined by tapered tip 30. The ejected material then traverses passage 70 passing through filter apertures 80 of filter member 74 before being received by syringe assembly 212. As the adipose tissue is forced through the appropriate size filter apertures 80, the connective matrix is disrupted without exposing the associated identifiable cellular components to excessive shearing forces. This, in turn, lowers the viscosity of the collected material allowing contaminants to be more easily removed as well as improving the subsequent digestion of the sample and increasing the ultimate yield of endothelial cells. As the filtered, harvested adipose tissue enters syringe assembly 212 through tapered tip 230 positive displacement forces plunger 228 toward the rear of hollow tube 218. Of course, this procedure may be repeated by reversing the sequence of events to move the tissue from syringe assembly 212 to syringe assembly 12.

The improved yield of microvascular endothelial cells provided by the methods of the present invention is illustrated in the following nonlimiting example.

EXAMPLE 1

Human adipose tissue was collected from the thigh of a female Caucasian. Four different commercially available cannulas having apertures of various sizes and configurations were used to withdraw the fat from the thigh with the harvesting procedure taking place approximately thirty to sixty minutes prior to the experiment. Then samples collected by each type of cannula were then processed separately.

In each case the adipose tissue was briefly rinsed with Dulbecco's phosphate buffered saline. One of the samples of the harvested material was then homogenized by running the tissue between two syringes having a filter member with 1 mm filter apertures interposed between them. 10 grams of the respective fat sample and 10 mls of a collagenase solution (4 mg/ml, Boehringer Mannheim) were then combined in 50 ml Erlenmeyer flasks and placed in a shaker to incubate at 37° C. for twenty minutes at 100 cycles per minute.

The resulting digestion slurry was then poured into 15 ml conical centrifuge tubes and spun at 1800 rpm for seven minutes.

The endothelial cells and red blood cells precipitated at the bottom of conical centrifuge tubes. Dark collagenase solution formed a middle layer and the nonsoluble fat and associated adipose tissue formed a plug on top of the centrifuge tube. Both the dark collagenase solution and the fat were discarded.

The endothelial cell pellets were resuspended using 10 ml of 0.1% bovine serum albumin in Dulbecco's phosphate buffered saline, pooled in a new sterile conical centrifuge tube and spun at 1800 rpm for four (4) minutes. The supernatant was discarded and the endothelial cell pellets were resuspended with 14% human serum in Plasma-Lyte® (Baxter Healthcare Corporation) an FDA-approved medium for sodding with human blood serum.

The final volume of this solution in each case was approximately 9 ml. 0.2 ml of each resulting endothelial cell suspensions were diluted to 20 ml with Isoton® solution (Baxter Scientific Products). The cell yield and cell sizes in each suspension were determined using a Coulter Multisizer II. The cell yield was defined as the number of cells (larger than 7.78 µm) recovered per unit gram of fat. The yield of cells was used as the index of suitability of the design although cell viability was not studied in detail at this time. The adherence of the isolated cells on the well plate was examined only occasionally with reasonably good results.

The results of different syringe and cannula configurations are shown in Table 1 immediately below.

TABLE 1

| Type of Syringe/ Cannula | Cell Yield (No. of Cells/g fat) |
|---|---|
| Catheter tip/ 3.7 mm Mercedes | $1.12 \times 10^6$ |
| Catheter tip/ 3.7 mm Mercedes, 4 × filter | $1.60 \times 10^6$ |
| Toomey-type/ 3.0 mm Mercedes | $2.13 \times 10^6$ |
| Luer lock/ 1.5 mm luer lock | $1.58 \times 10^6$ |
| Toomey-type/ 3.00 mm Curret Special | $1.15 \times 10^6$ |

These data clearly show the improvement in identifiable cell yield through the use of the methods of the present invention. In particular, the results illustrate that the selection of an appropriate aperture size and configuration can increase the yield of microvascular endothelial cells from a given source of adipose tissue. For example, use of the Curret Special having a 3 mm diameter and rather rounded apertures only yielded approximately half of the viable cellular components obtained using a Mercedes having a 3 mm diameter and apertures with well-defined tissue cutting edges. Moreover, it is important to note that the diameter of the cannula alone is not the determinative criteria for increasing cell yields. This is illustrated by the fact that the use of either a 3.7 mm Mercedes or a 3 mm Curret Special only provided approximately 70% of the viable cells provided by a 1.5 mm Luer lock cannula having apertures with better tissue disruptive capabilities. Finally, the data show that homogenizing the harvested adipose tissue in accordance with the teachings of the present invention can substantially increase microvascular endothelial cell yields. For example, when samples are collected using identical 3.7 mm Mercedes cannula, homogenizing the adipose tissue by passing it four times through a filter member having 1 mm filter apertures increased the yield of viable cells by over 40%. Such increases in cell yields can easily prove to be the difference between successful endothelialization and incomplete coverage of the synthetic graft which may lead to the formation of life-threatening clots.

Those skilled in the art will further appreciate that the present invention may be embodied in other specific forms without departing from the spirit or central attributes thereof. In that the foregoing description of the present invention discloses only exemplary embodiments thereof, it is to be understood that other variations are recognized as being within the scope of the present invention. Accordingly, the present invention is not limited to the particular embodiments which have been described in detail herein. Rather, reference should be made to the appended claims to define the scope and content of the present invention.

What is claimed is:

1. A method of collecting fat tissue from a patient, said method comprising the steps of:

providing an elongated tubular cannula having a distal tip end and an opposite proximal end, a lumen extending in said cannula, and an aperture opening outwardly from said lumen on said cannula adjacent to said distal tip end and defining a tissue cutting edge surface;

inserting said cannula into a patient so that said aperture contacts fat tissue;

cutting said fat tissue with said tissue cutting edge surface;

creating a suction force in said lumen to draw said fat tissue from the patient through said aperture into said lumen;

selectively controlling the amount of suction to said lumen; and collecting said fat tissue from said lumen into a collection chamber, wherein said collection chamber includes an entrance port through which said fat tissue passes from said lumen in the step of collecting, said method further comprising the step of discharging said fat tissue from said collection chamber through said entrance port and through a homogenizing member having apertures with cutting edge surfaces and sized to lower the viscosity of the fat tissue by disrupting a connective matrix without exposing cellular components within said fat tissue to excessive shearing forces.

2. The method of claim 1, wherein said collection chamber comprises a syringe having a plunger, and wherein said step of selectively controlling the amount of suction to said lumen comprises manipulating said plunger.

3. The method of claim 2, further comprising the step of providing the proximal end of said cannula with means for retaining the plunger in a withdrawn position.

4. The method of claim 1, wherein said apertures have a diameter of about 0.2 to 3.0 mm.

5. The method of claim 1 further comprising the step of passing said fat tissue from said collection chamber through said homogenizing member into a second syringe.

6. The method of claim 1 further comprising the step of coating the homogenizing member with parylene.

7. The method of claim 1 further comprising the step of providing a plurality of apertures opening outwardly from said lumen on said cannula adjacent to said distal tip end, said apertures being elongated in a direction along the length of said cannula, wherein each aperture further comprises opposite distal and proximal ends, and opposite side edges, and wherein said distal and proximal ends, and opposite side edges of each aperture comprise a tissue cutting edge surface.

8. The method of claim 1, wherein said aperture is elongated in a direction along the length of the cannula, and the length of said aperture is about three times its width.

9. A method for homogenizing fat tissue obtained from a patient prior to digestion of said fat tissue, said method comprising the steps of:

obtaining fat tissue from a patient, said fat tissue comprising microvascular endothelial cells;

disposing said fat tissue in a collection container comprising a first port;

positioning a planar homogenizing member comprising a plurality of apertures adjacent to said first port, wherein said plurality of apertures comprise at least one tissue cutting edge surface;

discharging said fat tissue from said collection container first port in a first direction generally normal to said planar homogenizing member through said plurality of apertures, so that said tissue cutting edge surface of said plurality of apertures cuts said fat tissue so as to free said endothelial cells;

receiving said fat tissue discharged through said homogenizing member in a receiving container through a second port; and discharging said fat tissue received in said receiving container through said second port in a second direction opposite the first direction and generally normal to said planar homogenizing member through said plurality of apertures into said collection container.

10. The method of claim 9, further comprising the step of discharging said fat tissue from said collection container in said first direction through said plurality of apertures by use of a syringe.

11. The method of claim 10, further comprising the step of discharging said fat tissue from said receiving container in said second direction through said plurality of apertures by use of a syringe.

12. The method of claim 10, wherein said collection container is formed by said syringe, and said step of obtaining comprises withdrawing fat tissue from the patient using said syringe.

13. The method of claim 9, wherein each of said apertures has a diameter of between about 0.2 mm and 3.0 mm.

14. The method of claim 9, further comprising the step of coating the homogenizing member with parylene.

15. The method of claim 9, further comprising repeating the step of discharging said fat tissue from said collection container to said receiving container.

16. The method of claim 15, further comprising repeating the step of discharging said fat tissue from said receiving container to said collection container.

17. The method of claim 9, further comprising the step of discharging said fat tissue from said receiving container in said second direction through said plurality of apertures by use of a syringe.

18. The method of claim 9, further comprising the steps of:

coupling said collection and receiving containers using a hub assembly attached to both said first and second ports; and wherein said step of positioning includes mounting said homogenizing member within said hub assembly.

19. The method of claim 18, wherein said collection chamber is formed by a syringe having a plunger, the step of discharging said fat tissue from said collection container in said first direction being accomplished by depressing the collection chamber syringe plunger, and said receiving chamber is formed by a syringe having a plunger, the step of discharging said fat tissue from said receiving container in said second direction being accomplished by depressing the receiving chamber syringe plunger.

* * * * *